US012800506B2

(12) United States Patent
Goda et al.

(10) Patent No.: US 12,800,506 B2
(45) Date of Patent: Nov. 17, 2026

(54) MANUFACTURING METHOD FOR SENSOR BOARD, SENSOR BOARD, SENSOR SYSTEM, AND RAMAN SCATTERING DETECTION METHOD

(71) Applicant: LucasLand, Co. Ltd., Tokyo (JP)

(72) Inventors: Keisuke Goda, Kanagawa (JP); Tinghui Xiao, Kanagawa (JP); Limei Liu, Kanagawa (JP); Kotaro Hiramatsu, Kanagawa (JP)

(73) Assignee: LucasLand, Co. Ltd., Tokyo (JP)

( * ) Notice: Subject to any disclaimer, the term of this patent is extended or adjusted under 35 U.S.C. 154(b) by 120 days.

(21) Appl. No.: 18/552,265

(22) PCT Filed: Mar. 25, 2022

(86) PCT No.: PCT/JP2022/014219
§ 371 (c)(1),
(2) Date: Sep. 25, 2023

(87) PCT Pub. No.: WO2022/210317
PCT Pub. Date: Oct. 6, 2022

(65) Prior Publication Data

US 2024/0167960 A1 May 23, 2024

(30) Foreign Application Priority Data

Mar. 29, 2021 (JP) ................................ 2021-055087

(51) Int. Cl.
*G01N 21/65* (2006.01)
*A61B 5/00* (2006.01)

(52) U.S. Cl.
CPC ............. *G01N 21/658* (2013.01); *A61B 5/00* (2013.01); *G01N 21/65* (2013.01)

(58) Field of Classification Search
CPC ......... G01N 21/658; G01N 21/65; A61B 5/00
See application file for complete search history.

(56) References Cited

U.S. PATENT DOCUMENTS 8,932,384 B1 * 1/2015 Hernandez-Rivera ....................... B22F 1/0547 75/741
2009/0130778 A1 * 5/2009 Kalgutkar ............... C23C 14/20 436/526

(Continued)

FOREIGN PATENT DOCUMENTS

JP 2017-517008 A 6/2017
JP 2019-504290 A 2/2019
JP 2020-012724 A 1/2020

OTHER PUBLICATIONS

Moser, H.O., Bahou, M., Casse, B.D.F. et al. Making and measuring nanostructures: Nanoscience and technology at the Singapore synchrotron light source. Crystallogr. Rep. 51 (Suppl 1), S170âS182 (2006), (Year: 2006).*

(Continued)

*Primary Examiner* — Tarifur R Chowdhury
*Assistant Examiner* — Carlos Perez-Guzman
(74) *Attorney, Agent, or Firm* — Rimon P.C.

(57) ABSTRACT

A sensor system includes: a sensor substrate having a metal nanomesh structure attachable to a surface of an object or a biological organism; a light source configured to emit light toward the sensor substrate; and a detector configured to detect surface-enhanced Raman-scattered light from molecules adsorbed on the metal nanomesh structure, by light emission from the light source. A method for fabricating a sensor substrate includes: preparing a mesh fiber sheet made of a given material by electrospinning; forming a metal layer on the mesh fiber sheet by a prescribed film formation method; and removing the mesh fiber sheet using liquid that dissolves the given material to obtain the sensor substrate having a metal nanomesh structure.

10 Claims, 9 Drawing Sheets

(56) References Cited

U.S. PATENT DOCUMENTS

| | | | | |
|---|---|---|---|---|
| 2012/0058697 | A1 | 3/2012 | Strickland et al. | |
| 2016/0069811 | A1* | 3/2016 | Rabolt | C01B 32/50<br>423/437.2 |
| 2016/0146737 | A1 | 5/2016 | Kim et al. | |
| 2017/0030836 | A1 | 2/2017 | Kim | |
| 2017/0102334 | A1 | 4/2017 | Zaretski et al. | |
| 2020/0323453 | A1* | 10/2020 | Lee | H05K 1/118 |
| 2022/0136972 | A1* | 5/2022 | Lee | C12Q 1/68<br>435/5 |

OTHER PUBLICATIONS

International Search Report issued in corresponding International Patent Application No. PCT/JP2022/014219, dated Jun. 14, 2022, w/ English Translation.

Song, et al., "Fabrication of a highly sensitive surface-enhanced Raman scattering substrate for monitoring the catalytic degradation of organic pollutants," Journal of Materials Chemistry A. 2015, vol. 3/Iss. 25, pp. 13556-13562.

Amarjargal, A., et al., "Simple fabrication of Ag nanoparticle-impregnated electrospun nanofibres as SERS substrates," Bull Mater Sci 38, 267-270 (2015).

* cited by examiner

MANUFACTURING METHOD FOR SENSOR BOARD, SENSOR BOARD, SENSOR SYSTEM, AND RAMAN SCATTERING DETECTION METHOD

CROSS REFERENCE TO RELATED APPLICATIONS

This application is the U.S. National Phase under 35 U.S.C. § 371 of International Application No. PCT/JP2022/014219, filed on Mar. 25, 2022, which claims the benefit of Japanese Application No. 2021-055087, filed on Mar. 29, 2021, the entire contents of each are hereby incorporated by reference.

TECHNICAL FIELD

The present invention relates to a method for fabricating a sensor substrate used to measure Raman-scattered light, a sensor substrate, a sensor system, and a method for detecting Raman-scattered light.

BACKGROUND ART

Surface-enhanced Raman spectroscopy (SERS) is a technique that enhances Raman scattering by molecules adsorbed on metal surfaces with nanostructures, allowing ultrasensitive measurements of molecular structure information. SERS further enables environmentally insensitive, noninvasive and safe measurements. Conventional SERS measures Raman scattering by dropping a sample on metal nanoparticles which are applied on a substrate such as a glass substrate (e.g., see Patent Literature 1).

CITATION LIST

Patent Literature

Patent Literature 1: Japanese Laid-Open Patent Publication No. 2020-012724

SUMMARY OF INVENTION

Technical Problem

Unfortunately, the conventional SERS measurements employ rigid substrates as sensor substrates such as glass substrates, which are not attachable to non-flat surfaces of various objects or biological organisms. This precludes biological monitoring and analysis of a small amount of sample adsorbed on the non-flat surfaces, and thus limits the possible applications.

The invention has been made in view of the foregoing, and an object of the invention is to provide a method for fabricating a sensor substrate that is attachable to surfaces of various objects and biological organisms and used to measure surface-enhanced Raman-scattered light, the sensor substrate, a sensor system, and a method for detecting Raman-scattered light.

Solution to Problem

A method for fabricating a sensor substrate according to the invention is a method for fabricating a sensor substrate used to measure surface-enhanced Raman-scattered light. The method includes: preparing a mesh fiber sheet made of a given material by electrospinning; forming a metal layer on the mesh fiber sheet by a prescribed film formation method; and removing the mesh fiber sheet using liquid that dissolves the given material to obtain the sensor substrate having a metal nanomesh structure.

A sensor substrate according to the invention has a metal nanomesh structure attachable to a surface of an object or a biological organism. The sensor substrate is used to measure surface-enhanced Raman-scattered light from molecules adsorbed on the metal nanomesh structure.

A sensor system according to the invention includes: a sensor substrate having a metal nanomesh structure attachable to a surface of an object or a biological organism; a light source configured to emit light toward the sensor substrate; and a detector configured to detect surface-enhanced Raman-scattered light from molecules adsorbed on the metal nanomesh structure, by light emission from the light source.

A method for detecting Raman-scattered light according to the invention includes: emitting light from a light source toward a sensor substrate having a metal nanomesh structure attached to a surface of an object or a biological organism; and detecting, by a detector, surface-enhanced Raman-scattered light from molecules adsorbed on the metal nanomesh structure, by light emission from the light source.

Advantageous Effects of Invention

According to the invention, by attaching a sensor substrate having a metal nanomesh structure to surfaces of various objects or biological organisms, it is possible to detect surface-enhanced Raman-scattered light.

DESCRIPTION OF EMBODIMENTS

Exemplary embodiments of the invention will be described below with reference to the drawings. The same reference signs are used to designate the same or similar elements throughout the drawings.

Method for Fabricating Sensor Substrate

A method for fabricating a sensor substrate used to measure surface-enhanced Raman-scattered light will be described with reference to FIGS. 1, 2A to 2C, and 3A to 3C. The sensor substrate of some embodiments is fabricated in the following three main steps:

(i) Step of preparing a mesh fiber sheet;

(ii) Step of forming a metal layer; and (iii) Step of obtaining a metal nanomesh structure.

Steps (i) to (iii) will be detailed below.

(i) Step of Preparing a Mesh Fiber Sheet

Figure 1:
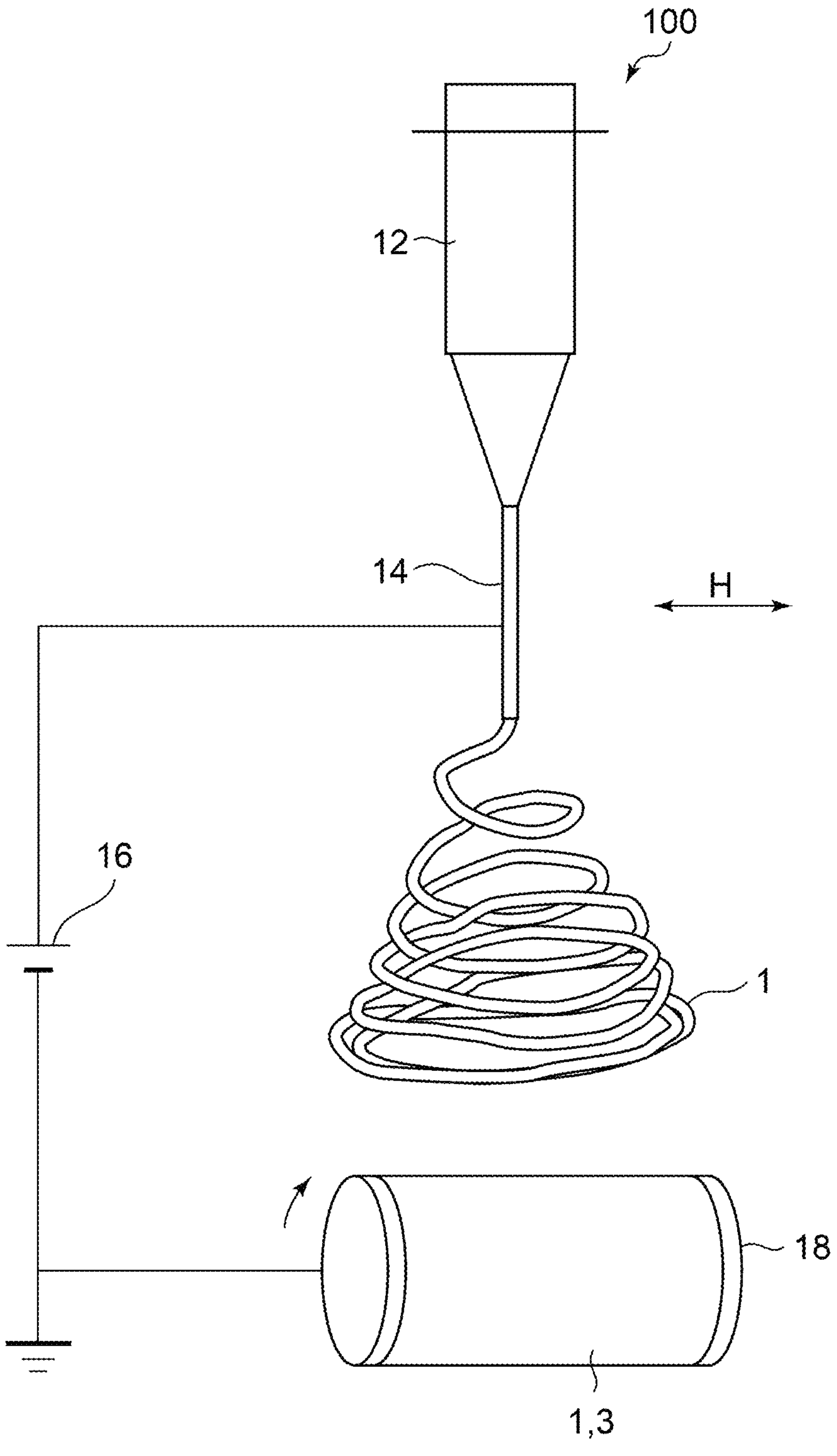
FIG. 1 is a schematic view of a configuration of an electrospinning device.

The mesh fiber sheet is prepared by electrospinning. FIG. 1 shows a configuration of an electrospinning device 100 for preparing the mesh fiber sheet. The electrospinning device 100 includes a syringe 12, a nozzle 14, a high-voltage power supply 16, and a collector 18.

Solution of a material of nanofibers 1 is introduced into the syringe 12. In some embodiments, polyvinyl alcohol (PVA) is employed as the material of the nanofibers 1. Alternative materials may be employed, such as water-soluble polymer other than PVA, as long as the nanofibers 1 are obtained by electrospinning and dissolvable in liquid.

The nozzle 14 is provided at the tip of the syringe 12 and connected to the high-voltage power supply 16. When a voltage is applied to the nozzle 14 from the high-voltage power supply 16, the PVA solution in the syringe 12 is ejected from the nozzle 14.

The high-voltage power supply 16 is connected to the nozzle 14 and the collector 18 to apply a preset direct voltage (e.g., 10 kV to 30 kV) between the nozzle 14 and the collector 18. Although FIG. 1 shows that the nozzle 14 and the collector 18 serve as a positive electrode and a negative electrode, respectively, the polarity of the electrodes may be interchangeable.

The collector 18 is a drum collector which is rotatable around its axis. The collector 18 is disposed separately from the nozzle 14 such that the axial direction (longitudinal direction) of the collector 18 is perpendicular to a longitudinal direction of the nozzle 14.

Figure 2A:
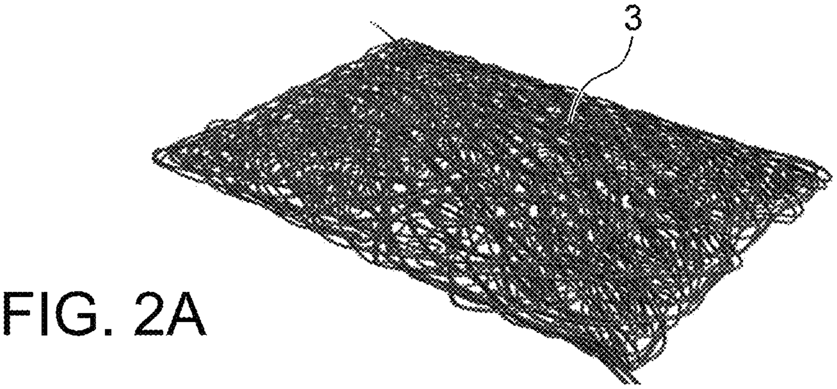
FIG. 2A is a schematic view of a mesh fiber sheet prepared by the electrospinning device.

When the voltage is applied between the nozzle 14 and the collector 18 by the high-voltage power supply 16, the PVA solution is ejected from the nozzle 14 toward the collector 18. The solvent in the PVA solution is volatilized to obtain nanoscale fibers (nanofibers 1) by the time the PVA solution reaches the collector 18, and the nanofibers 1 are deposited on a surface of the collector 18. While the collector 18 is rotating around its axis, the nanofibers 1 are wound onto the surface of the collector 18 and intertwined to form a mesh fiber sheet 3 as shown in FIG. 2A. The nanofibers 1 constituting the mesh fiber sheet 3 have a diameter of preferably 1 nm to 100 μm, more preferably 30 nm to 2 μm, which are exemplary and not restrictive.

The syringe 12 and the nozzle 14 are movable along the axial direction of the collector 18. Therefore, by ejecting the PVA solution toward the collector 18 while moving the syringe 12 and the nozzle 14 back and forth along the axial direction of the rotating collector 18 (H direction shown in FIG. 1), it is possible to obtain a large-area mesh fiber sheet 3. The mesh fiber sheet 3 has an area of preferably 0.01 $mm^2$ to 1 $m^2$, more preferably 1 $mm^2$ to 0.04 $m^2$, which are exemplary and not restrictive.

Note that instead of the drum collector 18, a plate collector may be employed.

Figure 3A:
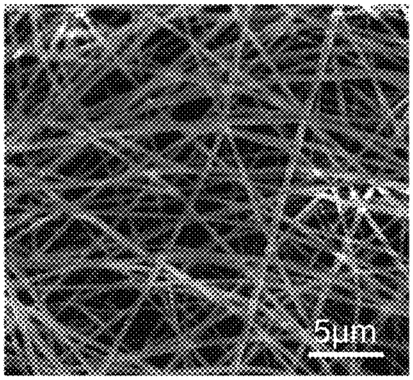
FIG. 3A is a microscope image of a mesh fiber sheet made of polyvinyl alcohol (PVA).

FIG. 3A shows an image of the mesh fiber sheet 3 made of PVA with a diameter of 500 nm, captured by a scanning electron microscope (SEM) (hereinafter referred to as a SEM image). A scale bar on the SEM image shown in FIG. 3A indicates 5 μm.

(ii) Step of Forming a Metal Layer

Figure 2B:
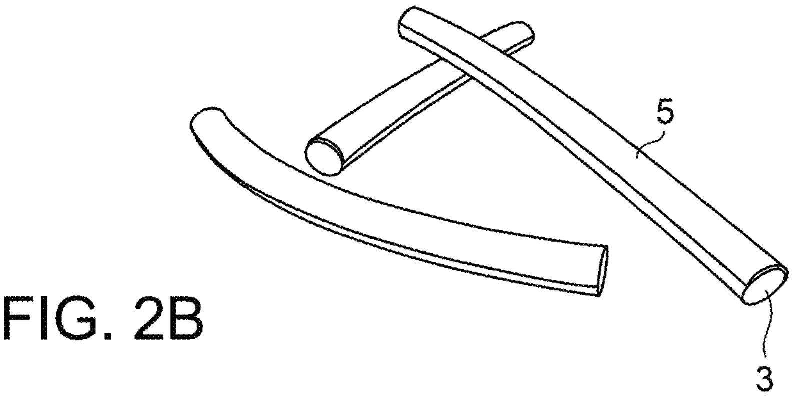
FIG. 2B is a schematic view of a composite structure in which a metal layer is formed on the mesh fiber sheet.

Next, a metal layer 5 is formed on the mesh fiber sheet 3 by a thermal-evaporation method. As shown in FIG. 2B, the metal layer 5 is a hollow semicylinder formed on a semicircular region of the fiber of the mesh fiber sheet 3. Note that alternative film formation methods other than the thermal-evaporation method may be used to form the metal layer 5 on the mesh fiber sheet 3.

The metal layer 5 is made of a pure metal or an alloy that exhibits a surface plasmon resonance. Examples of the metal of the metal layer 5 include gold (Au), silver (Ag), aluminum (Al), platinum (Pt), titanium (Ti), zinc (Zn), scandium (Sc), chromium (Cr), manganese (Mn), iron (Fe), cobalt (Co), nickel (Ni), copper (Cu), indium (In), tin (Sn), yttrium (Y), zirconium (Zr), niobium (Nb), molybdenum (Mo), ruthenium (Ru), rhodium (Rh), palladium (Pd), strontium (Sr), tungsten (W), cadmium (Cd), tantalum (Ta) or an alloy thereof, or indium tin oxide (ITO), indium zinc oxide (IZO), aluminum-doped zinc oxide (AZO), gallium indium zinc oxide (GIZO), zinc oxide (ZnO) or a mixture thereof. The metal layer 5 has a thickness of preferably 0.1 nm to 0.1 mm, more preferably 5 nm to 200 nm, which are exemplary and not restrictive.

Figure 3B:
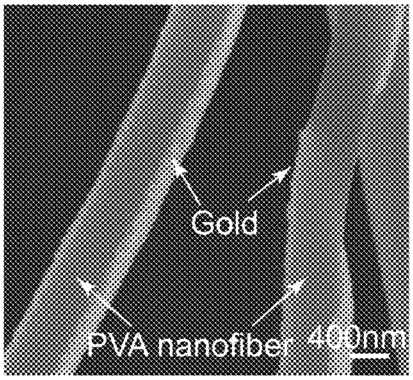
FIG. 3B is a microscope image of a composite structure in which a metal layer made of gold is formed on the mesh fiber sheet shown in FIG. 3A.

FIG. 3B shows a SEM image of a PVA/Au composite structure in which the metal layer 5 made of Au with a thickness of 150 nm is formed on the mesh fiber sheet 3 of FIG. 3A. A scale bar on the SEM image shown in FIG. 3B indicates 400 nm.

(iii) Step of Obtaining a Metal Nanomesh Structure

Figure 2C:
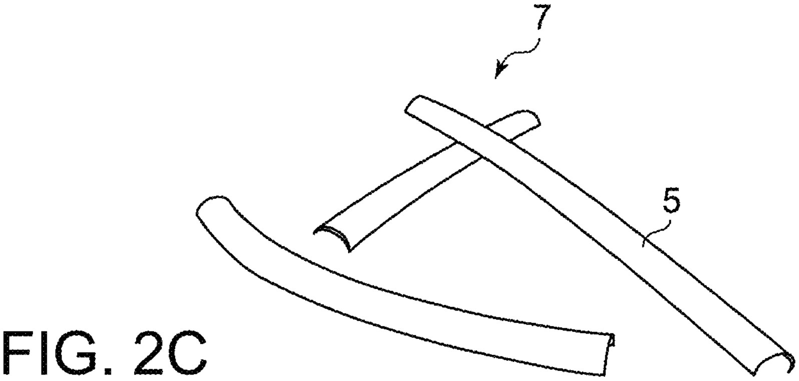
FIG. 2C is a schematic view of a metal nanomesh structure obtained by dissolving the mesh fiber sheet.

Finally, the mesh fiber sheet 3 is removed using liquid that dissolves the material of the mesh fiber sheet 3 but does not dissolve the metal layer 5, thereby obtaining a metal nanomesh structure 7 having the hollow semicylindrical metal layer 5 as shown in FIG. 2C.

For example, to remove the mesh fiber sheet 3 from the PVA/Au composite structure, first, water is sprayed on a target surface (e.g., human skin) to place the PVA/Au composite structure on the target surface, followed by spraying water again, but on the metal layer 5 to dissolve the mesh fiber sheet 3. A small amount of PVA left on a back side of the metal nanomesh structure 7 serves as an adhesive, allowing the metal nanomesh structure 7 to be attached on the target surface.

The metal nanomesh structure 7 has a thickness of preferably 1 nm to 100 μm, more preferably 30 nm to 100 μm, which are exemplary and not restrictive. The metal nanomesh structure 7 has the same area as that of the mesh fiber sheet 3, i.e., preferably 0.01 $mm^2$ to 1 $m^2$, more preferably 1 $mm^2$ to 0.04 $m^2$, which are exemplary and not restrictive. An average density of the metal of the metal nanomesh structure 7 is preferably 0.1 $g/cm^3$ to 50 $g/cm^3$, more preferably 0.1 $g/cm^3$ to 10 $g/cm^3$, which are exemplary and not restrictive.

Figure 3C:
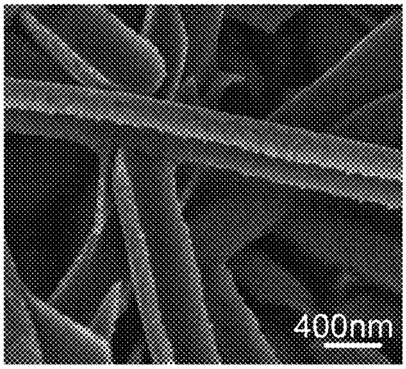
FIG. 3C is a microscope image of a metal nanomesh structure obtained by removing the mesh fiber sheet shown in FIG. 3B by spraying water.

FIG. 3C shows a SEM image of the metal nanomesh structure 7 obtained by removing the mesh fiber sheet 3 of FIG. 3B by spraying water. A scale bar on the SEM image shown in FIG. 3C indicates 400 nm.

Thus, the metal nanomesh structure 7 makes it possible to realize a flexible SERS sensor substrate which is attachable to a target surface in any shape. The fabrication method described above enables the fabrication of not only large-area sensor substrates but also sensor substrates in any shape.

If the diameter of the PVA mesh fiber sheet 3 is set to be about 500 nm and the thickness of the Au metal layer 5 is set to be about 150 nm, it is possible to maximize the effect of localized surface plasmon resonance (LSPR) on the metal nanomesh structure 7.

Figure 4:
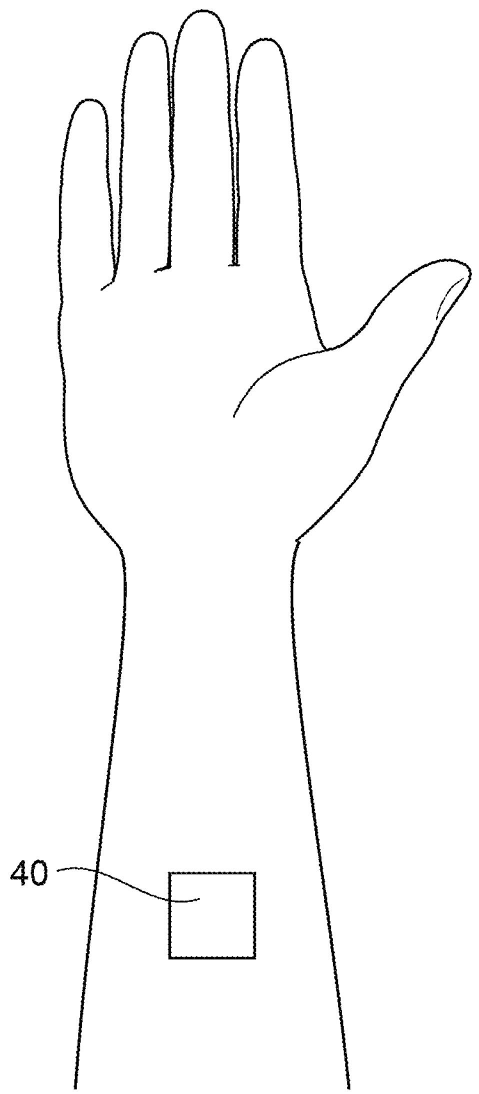
FIG. 4 is a schematic view of an example in which a sensor substrate of some embodiments is attached to human skin.

FIG. 4 shows an example in which a flexible sensor substrate 40 is attached to human skin (forearm). When the sensor substrate 40 is attached to the human skin, human sweat and other such biofluid adsorbed on the metal nanomesh structure 7 can be measured to grasp the health condition using a sensor system to be described later (See FIG. 5), which makes it possible to realize wearable sensors utilizing SERS.

Configuration of Sensor System

Figure 5:
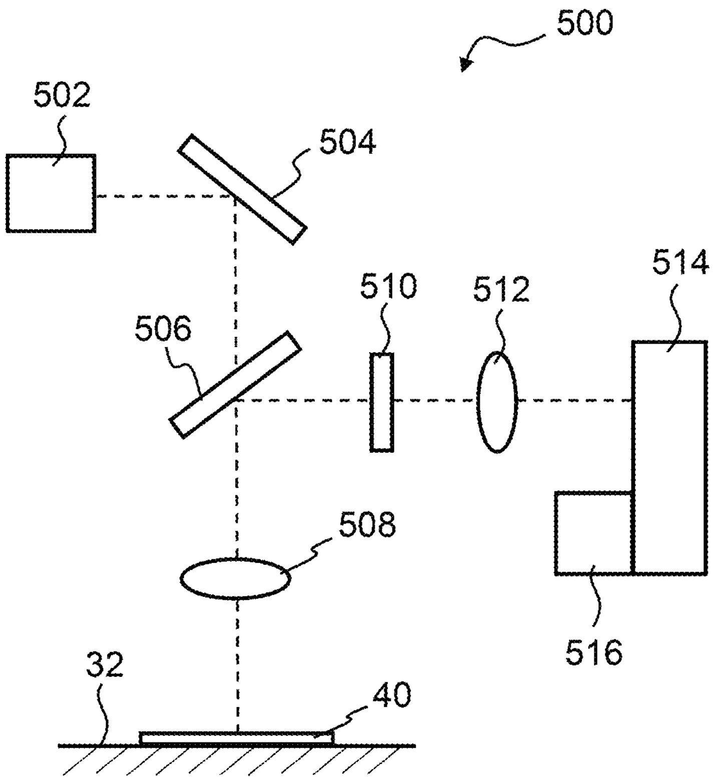
FIG. 5 is a schematic view of a configuration of a sensor system of some embodiments.

Next, a sensor system for measuring Raman scattering using the sensor substrate 40 will be described with reference to FIG. 5. As shown in FIG. 5, the sensor system 500 of some embodiments includes the sensor substrate 40 attached to a surface 32 of an object or a biological organism, a light source 502, a mirror 504, a half mirror 506, a lens 508, a filter 510, a lens 512, a spectrometer 514, and a detector 516.

The light source 502 emits continuous-wave (CW) semiconductor laser of single wavelength. Various wavelengths of laser may be employed depending on measurement targets.

The mirror 504 reflects an incident light from the light source 502 to change an optical axis. The reflected light from the mirror 504 is guided to the sensor substrate 40 through the half mirror 506 and the lens 508.

The half mirror 506 transmits part of the incident light from the light source 502 and reflects part of scattered light from the sensor substrate 40 (Rayleigh-scattered light, Raman-scattered light, and so on).

The lens 508 is located between the half mirror 506 and the sensor substrate 40, and the sensor substrate 40 is located at a focus position of the lens 508. The lens 508 focuses the transmitted light from the half mirror 506 onto the sensor substrate 40 to irradiate the sensor substrate 40. When the sensor substrate 40 is irradiated with light, the scattered light from the sensor substrate 40 is collimated by the lens 508 and incident on the half mirror 506. Specifically, surface-enhanced Raman-scattered light is produced from molecules adsorbed on the metal nanomesh structure 7 of the sensor substrate 40.

The filter 510 is a notch filter that removes the Rayleigh-scattered light from the reflected light from the half mirror 506 and transmits the Raman-scattered light.

At a focus position of the lens 512, an entrance of the spectrometer 514 is located. The lens 512 focuses the transmitted light from the filter 510 (i.e., Raman-scattered light) onto the spectrometer 514. The spectrometer 514 disperses the output light from the lens 512.

The detector 516 is located on an exit side of the spectrometer 514 to detect an intensity of the dispersed light from the spectrometer 514 and convert the detected intensity into an electrical signal. An example of the detector 516 includes, but is not limited to, a charge-coupled device (CCD) detector. Note that the detector 516 may be connected to a computer (not shown) that can collect and store measured data obtained by the detector 516.

Thus, it is possible to realize the SERS sensor system 500 in a simple configuration. The elements of the sensor system 500 except the sensor substrate 40 can be integrated with one another to provide a small handheld device.

Note that alternative configurations which are different from the sensor system 500 shown in FIG. 5 may be employed as long as they can measure Raman-scattered light from molecules adsorbed on the metal nanomesh structure 7 of the sensor substrate 40. For example, instead of the half mirror 506, a dichroic mirror with a wavelength-selective reflectance may be used. In addition, as the filter 510, a longpass filter may be used instead of the notch filter. Furthermore, instead of a spontaneous Raman spectroscopy system shown in FIG. 5, a coherent Raman spectroscopy system may be employed.

Next, measurements using the sensor system 500 (Examples 1 to 4) will be demonstrated with reference to FIGS. 6 to 9B.

Example 1

Figure 6:
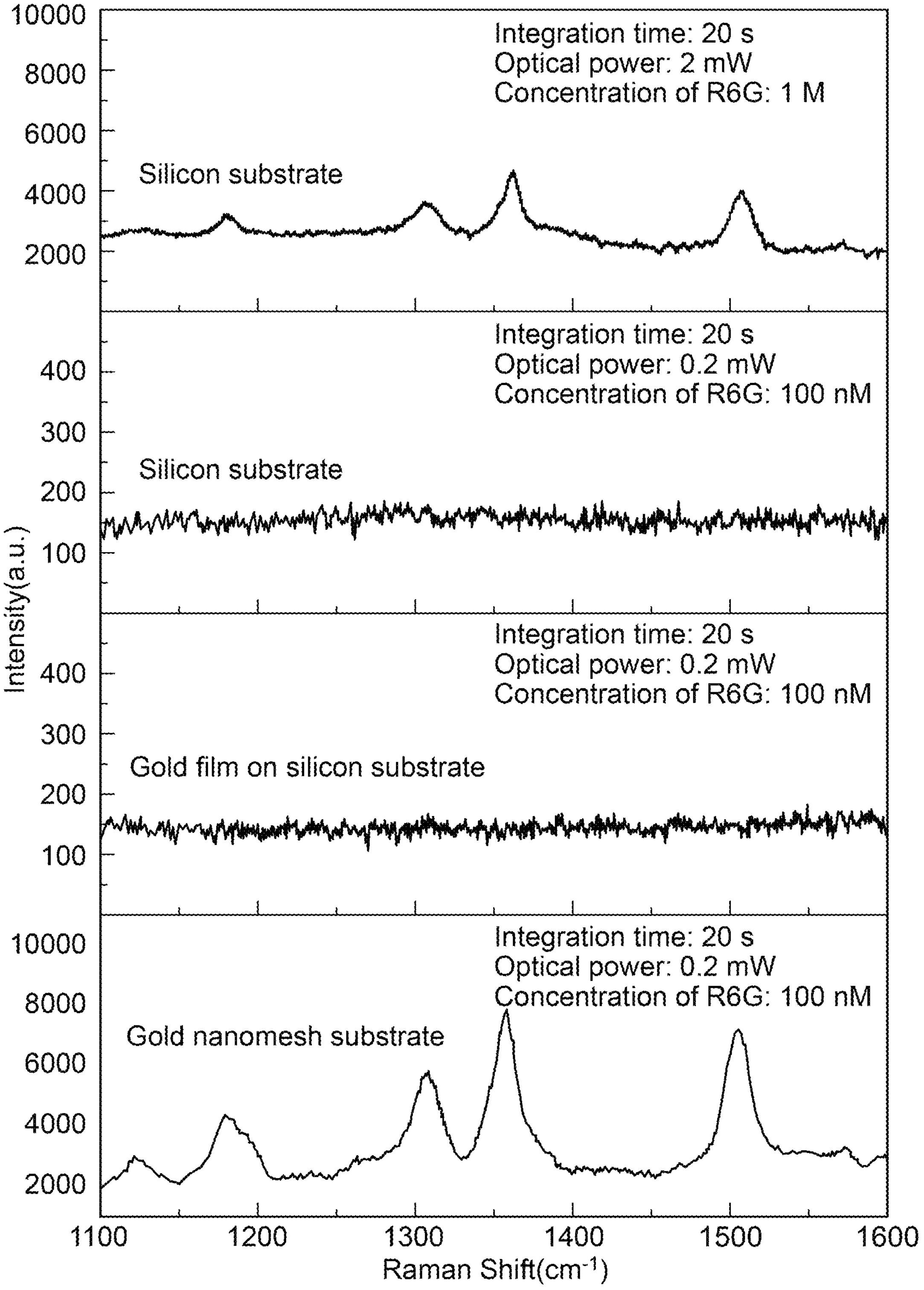
FIG. 6 is a graph of Raman spectra of rhodamine 6G (R6G) molecules on various types of substrates.

FIG. 6 shows Raman spectra of rhodamine 6G (R6G) molecules adsorbed on various types of substrates. The various types of substrates include silicon substrates (hereinafter referred to as a silicon sensor substrate), a sensor substrate in which a gold film with a thickness of 150 nm is disposed on a silicon substrate (hereinafter referred to as a gold film sensor substrate), and the sensor substrate 40 having the metal nanomesh structure 7 according to some embodiments.

Raman spectrum of an R6G solution at a concentration of 1M on the silicon sensor substrate is measured as a ground truth with an integration time of 20 seconds using a semiconductor laser with an excitation power of 2 mW at an excitation wavelength of 785 nm. As shown in a top graph of FIG. 6, Raman peaks can be clearly observed.

The second and third graphs from the top of FIG. 6 suggest that with a lower excitation power of 0.2 mW at a lower concentration of 100 nM of an R6G solution, Raman peaks disappear for both the silicon sensor substrate and the gold film sensor substrate.

Raman spectrum of R6G molecules on the sensor substrate 40 of some embodiments is measured under the same condition (i.e., excitation power: 0.2 mW; concentration of the R6G solution: 100 nM; and integration time: 20 seconds). As shown in a bottom graph of FIG. 6, Raman peaks can be clearly observed at around 1185 $cm^{-1}$, 1314 $cm^{-1}$, 1361 $cm^{-1}$, and 1509 $cm^{-1}$, and Raman signal enhancement is observed compared to the ground truth with a larger excitation power and a larger concentration of the R6G solution.

According to FIG. 6, an enhancement factor of a Raman-scattered light intensity for the metal nanomesh structure 7 of the sensor substrate 40 is found to be (2 mW/0.2 mW)×(1 M/100 nM)×(8000/4500)≈$10^8$ for R6G.

Example 2

Figure 7A:
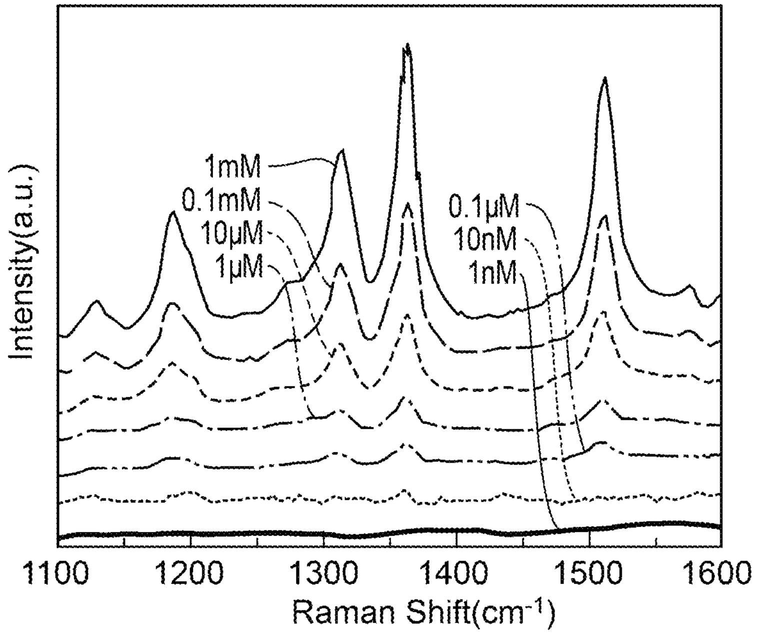
FIG. 7A is a graph of Raman spectra of R6G molecules on the sensor substrate obtained at different R6G concentrations.
Figure 7B:
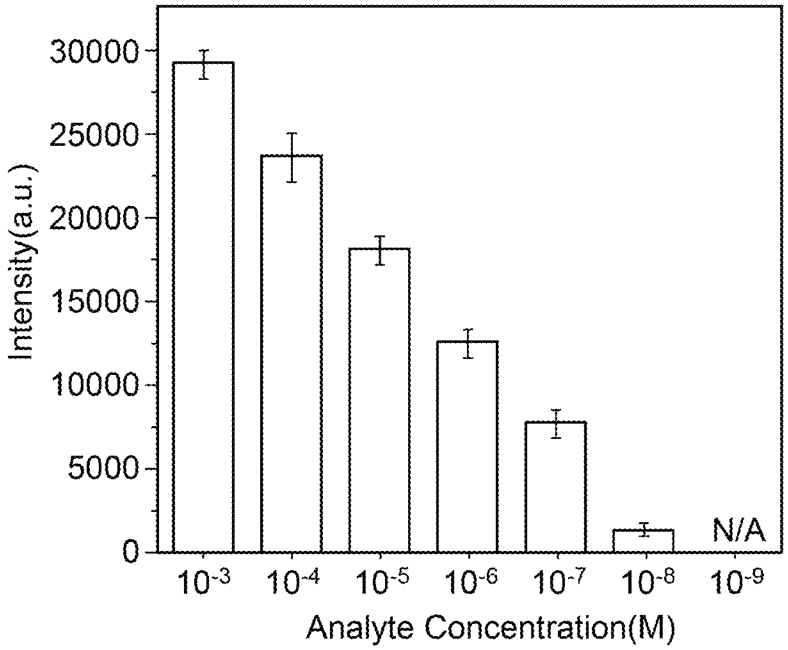
FIG. 7B is a graph of a relationship between R6G concentrations and intensities of Raman peaks at a Raman shift of 1361 $cm^{-1}$ shown in FIG. 7A.

FIG. 7A shows Raman spectra of R6G molecules on the sensor substrate 40 measured at different R6G concentrations for an integration time of 20 seconds using a semiconductor laser with an excitation power of 0.2 mW at an excitation wavelength of 785 nm. FIG. 7B shows a relationship between R6G concentrations and intensities of Raman peaks at a Raman shift of 1361 $cm^{-1}$ shown in FIG. 7A. FIGS. 7A and 7B suggest that the higher the R6G concentration, the larger the intensity of the Raman spectrum, and the lowest concentration at which the Raman peaks are detectable is about 10 nM (=$10^{-8}$ M).

Example 3

Figure 8A:
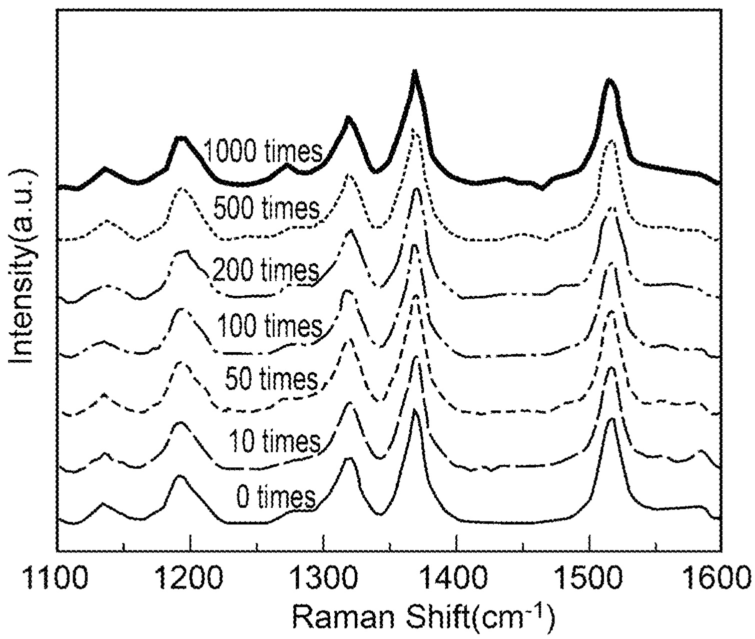
FIG. 8A is a graph of Raman spectra of R6G molecules on the sensor substrate for different number of cycles in a crumpling test on the sensor substrate.
Figure 8B:
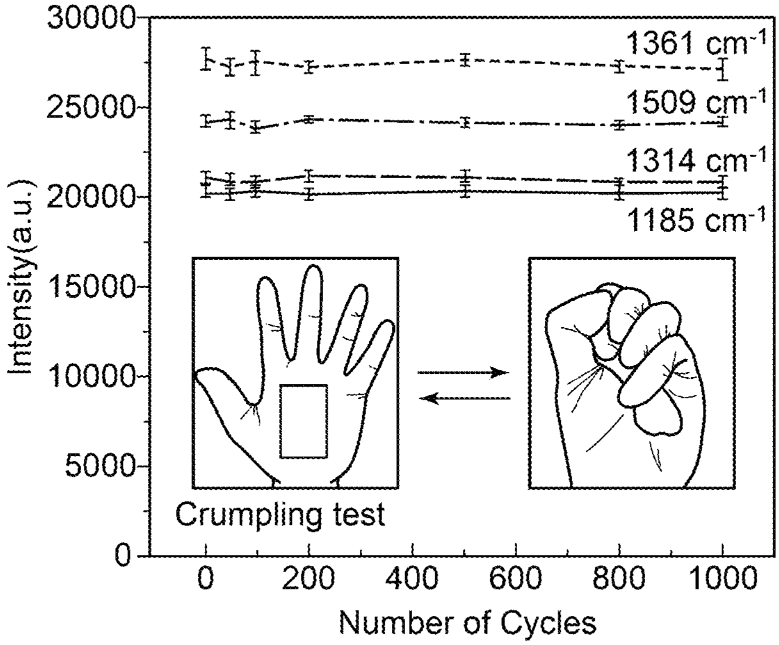
FIG. 8B is a graph of a relationship between the number of cycles in the crumpling test and intensities of Raman peaks shown in FIG. 8A.

Next, a flexibility test on the sensor substrate 40 will be demonstrated with reference to FIGS. 8A and 8B. A crumpling test is conducted by adhering the sensor substrate 40 to a palm of a hand glove and closing and opening the hand to crumple the sensor substrate 40 (See an inset of FIG. 8B).

In the crumpling test, 1000 cycles of closing and opening the hand are repeated. FIG. 8A shows Raman spectra of R6G molecules for different number of cycles: zero times, 10 times, 50 times, 100 times, 200 times, 500 times, and 1000 times. As shown in FIG. 8A, the Raman spectra exhibit no appreciable change even after 1000-cycle crumpling, and Raman peaks can be clearly observed.

FIG. 8B shows a relationship between the number of cycles in the crumpling test and intensities of four Raman peaks shown in FIG. 8A. As shown in FIG. 8B, the intensities of the Raman peaks of R6G molecules exhibit no appreciable change even after the 1000-cycle crumpling.

Example 4

Figure 9A:
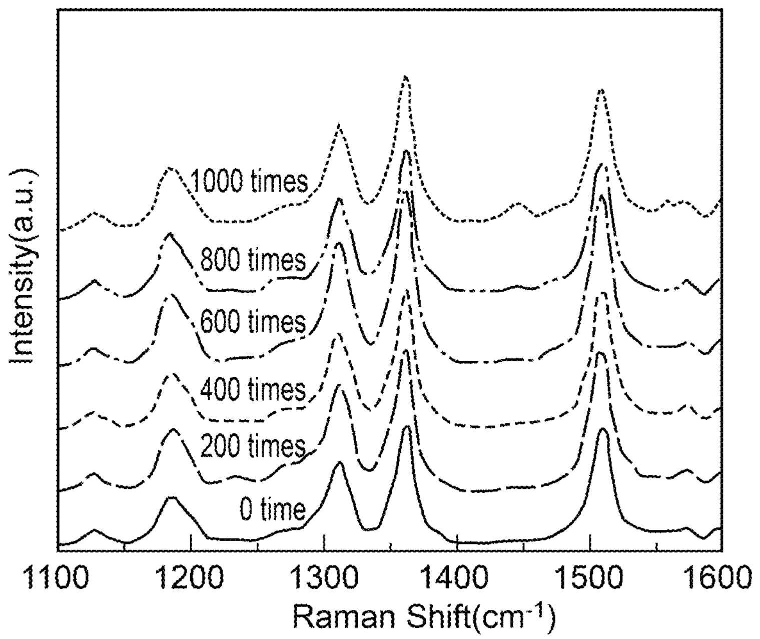
FIG. 9A is a graph of Raman spectra of R6G molecules on the sensor substrate for different number of cycles in a stretchability test on the sensor substrate.
Figure 9B:
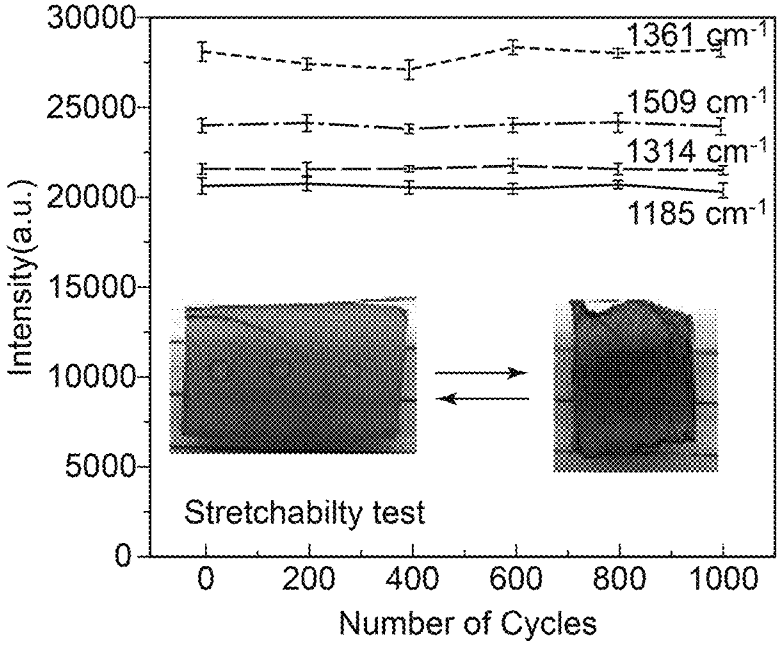
FIG. 9B is a graph of a relationship between the number of cycles in the stretchability test and intensities of Raman peaks shown in FIG. 9A.

Next, a stretchability test on the sensor substrate 40 will be demonstrated with reference to FIGS. 9A and 9B. The stretchability test is conducted by adhering the sensor substrate 40 to a 50% prestretched polydimethylsiloxane (PDMS) substrate and stretching and releasing the sensor substrate 40 together with the PDMS substrate (See an inset of FIG. 9B).

In the stretchability test, 1000 cycles of stretching and releasing are repeated. FIG. 9A shows Raman spectra of R6G molecules for different number of cycles: zero times, 200 times, 400 times, 600 times, 800 times, and 1000 times. As shown in FIG. 9A, the Raman spectra exhibit no appreciable change even after 1000-cycle stretching, and Raman peaks can be clearly observed.

FIG. 9B shows a relationship between the number of cycles in the stretchability test and intensities of four Raman peaks shown in FIG. 9A. As shown in FIG. 9B, the intensities of the Raman peaks of R6G molecules exhibit no appreciable change even after the 1000-cycle stretching.

As described above, the sensor substrate 40 of some embodiments can be adhered to an object or a biological organism to observe Raman-scattered light, indicating that the sensor substrate 40 has high flexibility, high stretchability, high adhesivity, and high biointegratability.

By adhering the sensor substrate 40 to surfaces of various objects and biological organisms in addition to the human arm, it is possible to achieve label-free and in situ sensing of diverse analytes at low concentrations (≈10 nM). For example, the sensor substrate 40 can be adhered to a human cheek and a contact lens to detect biomarkers in tears. In addition, the sensor substrate 40 can be adhered to a utility pole, a face mask, an elevator control panel, a door handle, a doorknob, a computer keyboard, and other such objects, which makes it possible to realize environmental monitoring and infection surveillance. Furthermore, the sensor substrate 40 can be adhered to fruits and vegetables to test pesticides and other such substances, which makes it possible to ensure food safety.

REFERENCE SIGNS LIST

1: Nanofibers
3: Mesh fiber sheet
5: Metal layer
7: Metal nanomesh structure
12: Syringe
14: Nozzle
16: High-voltage power supply
18: Collector
100: Electrospinning device
32: Surface
40: Sensor substrate
500: Sensor system
502: Light source
504: Mirror
506: Half mirror
508: Lens
510: Filter
512: Lens
514: Spectrometer
516: Detector

The invention claimed is:

1. A method for fabricating a sensor substrate used to measure surface-enhanced Raman-scattered light, the method comprising:
- preparing a mesh fiber sheet made of a given material by electrospinning, fibers constituting the mesh fiber sheet having a diameter of 1 nm to 100 μm;
- forming a metal layer on the mesh fiber sheet by a prescribed film formation method, an average density of a metal constituting the metal layer being 0.1 $g/cm^3$ to 50 $g/cm^3$; and
- removing the mesh fiber sheet using liquid that dissolves the given material to obtain the sensor substrate having a metal nanomesh structure.

2. The method according to claim 1, wherein the mesh fiber sheet has an area of 0.01 $mm^2$ to 1 $m^2$.

3. The method according to claim 1, wherein the metal layer has a thickness of 0.1 nm to 0.1 mm.

4. The method according to claim 1, wherein the metal layer is made of a pure metal or an alloy that exhibits a surface plasmon resonance.

5. The method according to claim 1, wherein
- the given material is polyvinyl alcohol, and
- the metal nanomesh structure is obtained by dissolving the mesh fiber sheet made of polyvinyl alcohol with water.

6. A sensor substrate having a metal nanomesh structure attachable to a surface of an object or a biological organism, the sensor substrate being used to measure surface-enhanced Raman-scattered light from molecules adsorbed on the metal nanomesh structure, wherein the metal nanomesh structure has a thickness of 30 nm to 100 μm, and wherein an average density of a metal constituting the metal nanomesh structure is 0.1 $g/cm^3$ to 50 $g/cm^3$.

7. The sensor substrate according to claim 6, wherein the metal nanomesh structure has an area of 0.01 $mm^2$ to 1 $m^2$.

8. The sensor substrate according to claim 6, wherein a metal constituting the metal nanomesh structure is a pure metal or an alloy that exhibits a surface plasmon resonance.

9. A sensor system, comprising:

the sensor substrate attachable to the surface of the object or the biological organism according to claim 6;

a light source configured to emit light toward the sensor substrate; and a detector configured to detect the surface-enhanced Raman-scattered light from the molecules adsorbed on the metal nanomesh structure, by light emission from the light source.

10. A method for detecting Raman-scattered light, comprising:

emitting light from a light source toward the sensor substrate having the metal nanomesh structure attached to the surface of the object or the biological organism according to claim 6; and detecting, by a detector, surface-enhanced Raman-scattered light from molecules adsorbed on the metal nanomesh structure, by light emission from the light source.

* * * * *